United States Patent
Bral (10) Patent No.: US 10,226,586 B2
(45) Date of Patent: Mar. 12, 2019

(54) MEANS AND METHOD TO PAINLESSLY PUNCTURE SKIN

(76) Inventor: Pourang Bral, Passaic, NJ (US)

( * ) Notice: Subject to any disclaimer, the term of this patent is extended or adjusted under 35 U.S.C. 154(b) by 1066 days.

(21) Appl. No.: 13/134,013

(22) Filed: May 26, 2011

(65) Prior Publication Data

US 2012/0302939 A1     Nov. 29, 2012

(51) Int. Cl.
    *A61M 5/42*     (2006.01)
    *A61N 1/36*     (2006.01)

(52) U.S. Cl.
    CPC .......... *A61M 5/422* (2013.01); *A61N 1/36021* (2013.01)

(58) Field of Classification Search
    CPC ...... A61M 5/3287; A61M 5/42; A61M 5/422; A61N 1/36021
    USPC ................ 604/20, 21, 22, 506, 512, 112
    See application file for complete search history.

(56) References Cited

U.S. PATENT DOCUMENTS

| | | |
|---|---|---|
| 1,561,116 A | 11/1925 | Silliman |
| 2,258,857 A | 11/1941 | McCann |
| 2,945,496 A | 7/1960 | Fosdal |
| 3,207,159 A | 9/1965 | Tatelsi |
| 3,308,823 A | 3/1967 | Peterson |
| 3,467,104 A | 9/1969 | Burbridge |
| 3,620,209 A | 11/1971 | Kravitz |
| 3,626,929 A | 12/1971 | Sanz et al. |
| 3,971,229 A | 7/1976 | Privas |
| 4,046,142 A | 9/1977 | Whitney |
| 4,309,989 A | 1/1982 | Fahim |
| 4,440,167 A | 4/1984 | Takehisa |
| 4,678,257 A | 6/1987 | Halpern |
| 4,710,172 A | 12/1987 | Jacklich et al. |
| 4,924,880 A | 5/1990 | O'Neill |
| 5,035,704 A | 7/1991 | Lambert |
| 5,088,925 A | 2/1992 | Mason |
| 5,171,225 A | 12/1992 | Sterrett |
| 5,271,522 A | 12/1993 | Ko |
| 5,431,655 A | 7/1995 | Meiker |
| 5,437,606 A | 8/1995 | Tsukamoto |
| 5,496,363 A | 3/1996 | Burgio |
| 5,496,383 A | 3/1996 | Burgio |
| 5,647,851 A | 7/1997 | Pokras |
| 5,680,872 A | 10/1997 | Sesekura et al. |

(Continued)

OTHER PUBLICATIONS http://www.ncbi.nlm.nih.gov/pmc/articles/PMC3001531/pdf/182e843. pdf Dec. 14, 2016, Reducing the Pain of Childhood Vaccination: an evidence-based clinical practice guideline Authors: Anna Faddio, Mary Appleton, Robert Borlolussi, Christine Chambers, Vinita Dubey, Scott Halperin, Anita Hanrahan, Moshe Sop, Donna Lockett, Noni MacDonald, Deana Midmer, Michael Rirder, Jeffrey Scott, Vibhuti Shah. Publication: CMAJ, vol. 182(18) p. E847.

(Continued)

*Primary Examiner* — Shefali D Patel (57) ABSTRACT

A means and a method is disclosed to diminish or eliminate pain associated with a sharp object penetrating skin, during such procedures as an injection, biopsy, or deriving a blood sample. To this end, repeated tapping, pressing, or rubbing is performed over the skin at or near a site of penetration of the sharp object in conjunction with applying electricity on the skin. The invention discloses a method of using a syringe or a lancet, with enhanced features, to provide local anesthesia at a site of penetration of a sharp object.

17 Claims, 5 Drawing Sheets

(56) References Cited

U.S. PATENT DOCUMENTS

| | | | |
|---|---|---|---|
| 5,728,050 A | 3/1998 | Lin | |
| 5,730,753 A | 3/1998 | Morita | |
| 5,839,895 A | 11/1998 | Fishburne | |
| 5,857,983 A | 1/1999 | Douglas et al. | |
| 5,873,844 A | 2/1999 | Campero | |
| 5,873,887 A | 2/1999 | King et al. | |
| 5,891,053 A | 4/1999 | Sesekura | |
| 5,927,976 A | 7/1999 | Wu | |
| 5,954,738 A | 9/1999 | LeVaughn et al. | |
| 5,964,718 A | 10/1999 | Duchon et al. | |
| 6,045,567 A | 4/2000 | Taylor et al. | |
| 6,063,039 A | 5/2000 | Cunningham et al. | |
| 6,066,103 A | 5/2000 | Duchon et al. | |
| 6,099,503 A | 8/2000 | Stradella | |
| 6,135,769 A | 10/2000 | Kwan | |
| 6,155,992 A | 12/2000 | Henning et al. | |
| 6,217,561 B1 | 4/2001 | Gibbs | |
| 6,231,531 B1 | 5/2001 | Lum | |
| 6,419,490 B1 | 7/2002 | Kitchings Weathers | |
| 6,454,743 B1 | 9/2002 | Weber | |
| 6,547,561 B2 | 4/2003 | Meller | |
| 6,599,272 B1 | 7/2003 | Hjertman | |
| 6,602,229 B2 | 8/2003 | Coss | |
| 6,626,887 B1 | 9/2003 | Wu | |
| 6,660,029 B2 | 12/2003 | VanSkiver | |
| 6,706,000 B2 | 3/2004 | Perez et al. | |
| 6,708,060 B1 | 3/2004 | Avrahami | |
| 6,902,554 B2 | 6/2005 | Huttner | |
| 7,386,349 B2 | 6/2008 | Davar | |
| 7,503,927 B1 | 3/2009 | Vetanze | |
| 7,803,128 B2 | 9/2010 | Christensen | |
| 2001/0049510 A1 | 12/2001 | Burr | |
| 2002/0082522 A1 | 6/2002 | Douglas | |
| 2002/0128600 A1* | 9/2002 | Nissels | A61M 5/425 604/131 |
| 2002/0147446 A1 | 10/2002 | Ein-Gal | |
| 2002/0188223 A1 | 12/2002 | Perez et al. | |
| 2002/0193861 A1 | 12/2002 | Harrison | |
| 2003/0036034 A1 | 2/2003 | Kay | |
| 2003/0078534 A1 | 4/2003 | Hochman | |
| 2003/0100888 A1 | 5/2003 | Spinello | |
| 2004/0015188 A1 | 1/2004 | Coulter | |
| 2004/0092843 A1 | 5/2004 | Kreiser et al. | |
| 2004/0230227 A1 | 11/2004 | Avrahami | |
| 2005/0149145 A1 | 7/2005 | Coulter | |
| 2005/0177071 A1* | 8/2005 | Nakayama et al. | 600/583 |
| 2005/0177201 A1 | 8/2005 | Freeman | |
| 2006/0105363 A1 | 5/2006 | Aravena | |
| 2006/0106363 A1 | 5/2006 | Aravena et al. | |
| 2006/0173386 A1 | 8/2006 | Lindquist | |
| 2006/0217636 A1 | 9/2006 | Braig | |
| 2007/0088385 A1 | 4/2007 | Perry | |
| 2007/0106342 A1* | 5/2007 | Schumann | A61H 39/002 607/46 |
| 2007/0197968 A1 | 8/2007 | Pongpalrochana | |
| 2007/0282400 A1 | 12/2007 | Gorham | |
| 2008/0039829 A1 | 2/2008 | Goldman | |
| 2008/0109049 A1 | 5/2008 | Schumann | |
| 2008/0125842 A1 | 5/2008 | Petitt | |
| 2008/0188779 A1* | 8/2008 | Vallero | 601/21 |
| 2009/0004628 A1 | 1/2009 | Knutson | |
| 2009/0118789 A1 | 5/2009 | Buhlmann | |
| 2010/0030299 A1 | 2/2010 | Covalin | |
| 2011/0022115 A1* | 1/2011 | Salzhauer | A61H 1/005 607/46 |
| 2011/0112477 A1 | 5/2011 | Bral | |
| 2012/0203137 A1* | 8/2012 | Neuman | A61B 5/1411 600/576 |
| 2015/0080850 A1 | 3/2015 | Bral | |

OTHER PUBLICATIONS

Refractory Period (Physiology), Internet Publication, last modified Nov. 2, 2016, at URL: https://en.wikipedia.org/wiki/Refractory_Period_(Physiology).

* cited by examiner

MEANS AND METHOD TO PAINLESSLY PUNCTURE SKIN

STATEMENT REGARDING FEDERALLY SPONSORED RESEARCH OR DEVELOPMENT

Not Applicable

THE NAME OF THE PARTIES TO A JOINT RESEARCH AGREEMENT

Not applicable.

INCORPORATION-BY-REFERENCE OF MATERIAL SUBMITTED ON A COMPACT DISC

Not Applicable

BACKGROUND OF THE INVENTION

As referred to in the U.S. patent application Ser. No. 12/590,658 by Pourang Bral, this inventor has discovered that applying electricity and physical stimulation to the vicinity of the injection site decreases or prevents the perception of pain of injection. This inventor has also discovered that physically stimulating the body near the site where electricity is applied lowers the uncomfortable perception of the shock of electrical current passing through the body. It also allows a more comfortable toleration of higher electrical voltages in the vicinity of the injection site. The higher voltage in turn provides a more profound temporary local anesthesia, and therefore, allows a better chance of a more comfortable or totally pain-free injection.

Furthermore, it was discovered by this inventor that post-injection soreness is minimized with the application of electricity to the vicinity of injection site in conjunction with an injection.

In the above mentioned application, I have disclosed a method of obtaining local anesthesia, as well as an injection assisting device, and a mechanized injecting device. It is my aim in the present application to disclose a novel manual skin-puncturing means and a method of using same to effect local anesthesia during procedures that require skin penetration.

Attempts have been made to use TENS electrical impulses along with vibration to effect local anesthesia, as described in US patent application #s: 20050149145 by Coulter, and 20080188779 by Vallero. Use of vibration requires a mechanized apparatus attached to a skin-puncturing means that adds weight and bulk to the means which are not preferred in many instances such as when one is traveling or carrying an automatic injecting device like an insulin pen. An aim of the present invention is to use manual tapping to effect local anesthesia obviating the need to carry a vibrating device.

This inventor has discovered that rubbing the skin before, during, or after applying an electrical current, such as a TENS stimulation, to the skin in the vicinity of the skin puncture site diminishes or prevents the pain associated with the skin puncture. Furthermore, this inventor has discovered that rubbing the skin near the site where electricity is applied lowers the uncomfortable perception of the shock of electrical current passing through the body. It also allows a more comfortable toleration of higher electrical voltages in the vicinity of the puncture site. The higher voltage in turn provides a more profound temporary local anesthesia, and therefore, allows a better chance of a more comfortable or totally pain-free invasion of the skin. In addition, I have discovered that rubbing and applying electricity to the vicinity of the puncture site reduces or prevents the post-op soreness in the area.

BRIEF SUMMARY OF THE INVENTION

It is an aim of this invention to disclose a means and a method of providing local anesthesia mainly with the use of a skin-puncturing means to painlessly penetrate the skin with a sharp object.

It is another object of this invention to provide a light and compact means to puncture the skin, and a method of using it, for purposes such as an injection, drawing a blood sample, or taking a tissue sample that corresponds to today's busy and on-the-run life style.

Furthermore, it is an aim of this invention to disclose a method of obtaining local anesthesia by applying an electrical current in conjunction with rubbing the skin at or near the puncture site.

DETAILED DESCRIPTION OF THE INVENTION

It has been shown that applying electrical impulses along with physical stimulation at or near the site of skin penetration diminishes or removes the pain associated with a breach in the skin barrier.

Figure 1:
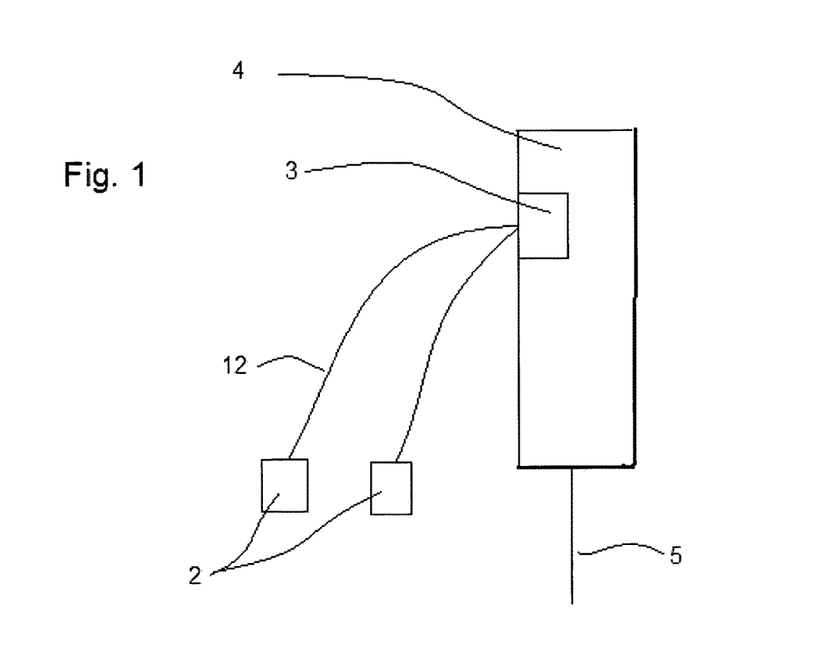
FIG. 1 illustrates a skin-puncturing means including a needle, a plurality of electrodes, and an electrical supply.

In a specific example of the invention, a skin-puncturing means 1 is disclosed, including a plurality of electrodes 2 transferring electrical impulses from an electric source 3, via a plurality of wires 12, to the skin in the vicinity of the skin puncture, while facilitating the tapping of, rubbing, or applying pressure on, the skin on or around the puncture site, FIG. 1.

In a specific example of the invention, said electric source 3 is a TENS, Transcutaneous Electrical Nerve Stimulation, device. In one example, said electrical source 3 is included in the body of said skin-puncturing means 1.

Figure 2:
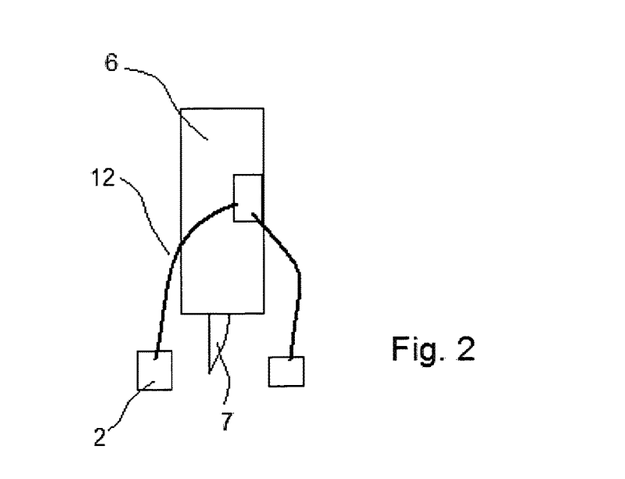
FIG. 2 illustrates a skin-puncturing means including a blade, a plurality of electrodes, and an electrical supply.

In a specific example of the invention, said skin-puncturing means 1 includes a sharp object to penetrate the skin. It may be a syringe 4 with a needle 5, FIG. 1, or a lancet 6 with a blade 7, FIG. 2.

In a specific example of the invention, said skin-puncturing means 1 is an auto-injection syringe such as an insulin pen.

Figure 3:
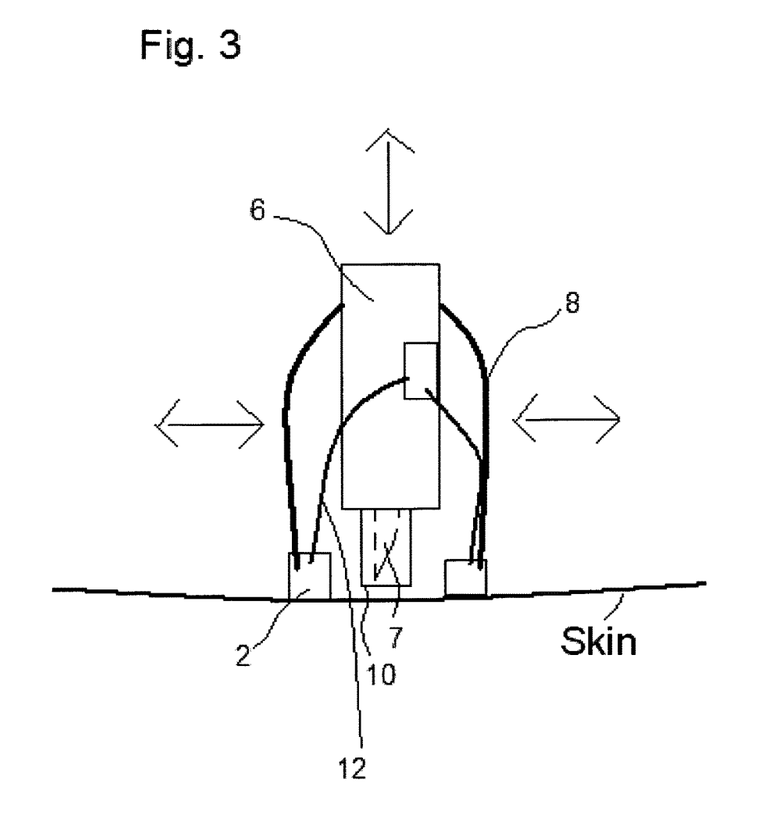
FIG. 3 illustrates a skin-puncturing means including a plurality of springs that help maintain an electrical contact between the electrodes and the skin while the skin-puncturing means moves away and towards the skin to provide a tapping or pressuring sensation on the skin.

In a specific example of the invention, said skin-puncturing means 1 acts as a means with which to tap or to apply pressure on the skin at or around the skin puncture site, FIG. 3. In one example, said plurality of electrodes 2 are attached to said skin-puncturing means 1 through a plurality of springs 8 that press said plurality of electrodes 2 to the skin, maintaining electrical contact between said electrodes 2 and the skin while the body of said skin-puncturing means 1 taps or applies pressure on the skin at or around the skin puncture site by repeatedly moving towards and away from the skin consecutively. In one example, said plurality of wires 12 form said plurality of springs 8.

Figures 9, 10:
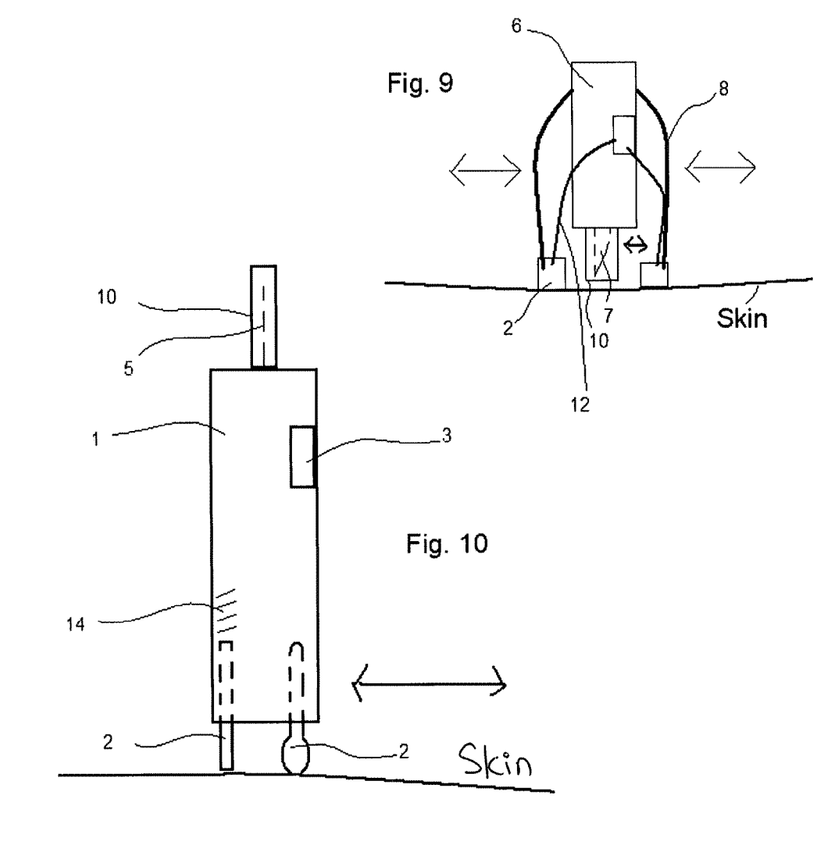
FIG. 9 illustrates a skin-puncturing means including a plurality of springs that help maintain an electrical contact between the electrodes and the skin while the skin-puncturing means moves side to side on the skin to provide a rubbing sensation on the skin. The electrodes are maintained stationary relative to the skin.
FIG. 10 illustrates a skin-puncturing means including a plurality of springs that help maintain an electrical contact between the electrodes and the skin. When the skin-puncturing means moves side to side on the skin, the electrodes rub against the skin and help provide local anesthesia. The skin-puncturing means can be pushed towards and touch the skin so that it can also help in rubbing the skin.

In a different example of the invention, said skin-puncturing means 1 acts as a means with which to rub the skin at or around the skin puncture site, FIG. 9. In one example, said plurality of electrodes 2 are attached to said skin-puncturing means 1 through a plurality of springs 8 that press said plurality of electrodes 2 to the skin, maintaining electrical contact between said electrodes 2 and the skin while the body of said skin-puncturing means 1 rubs the skin at or around the skin puncture site by repeatedly moving back and forth on the skin. In one example, said plurality of wires 12 form said plurality of springs 8. In another example, said plurality of electrodes are attached directly to said skin-puncturing means 1 and actually do the rubbing when said skin-puncturing means 1 moves back and forth repeatedly on the skin at or near the puncture site, FIG. 10.

Figure 8:
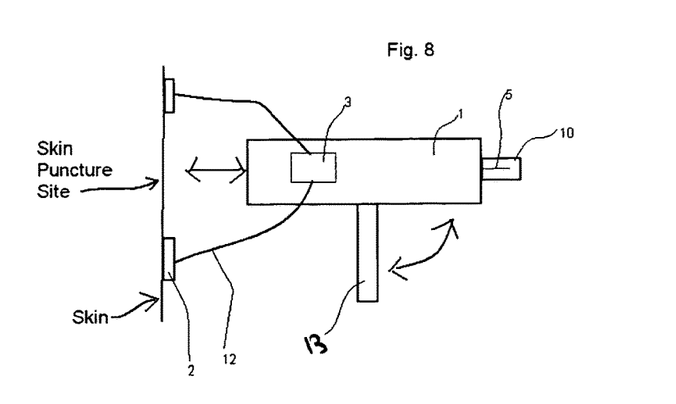
FIG. 8 illustrates a skin-puncturing means including a handle which is held onto by the person that administers the tapping on the skin.

In a different example of the invention, the body of said skin-puncturing means 1 is used to tap on the skin. To this end, however, a handle 13 can be used to tap said skin-puncturing means 1 repeatedly onto the skin in between a plurality of electrodes 2 that are electrically in contact with the skin, FIG. 8. For example, said handle 13 is retractable into or onto said skin-puncturing means 1 to give it a compact appearance.

Figure 4:
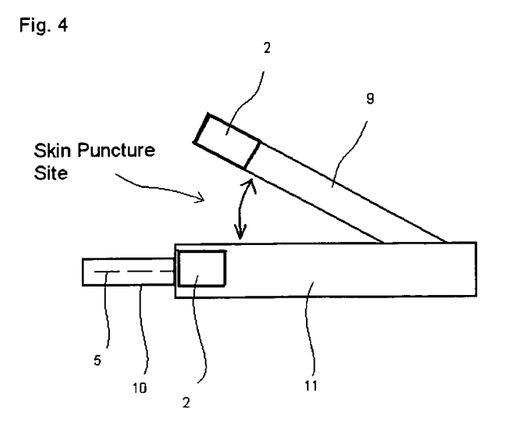
FIG. 4 shows an extension swiveling open from the main body of the skin-puncturing means, thereby forming a space on the skin between a plurality of electrodes that apply an electrical current to the skin. The space is used to tap, or apply pressure, directly on the skin at or near the puncture site.

In a specific example of the invention, said skin-puncturing means 1 includes a plurality of extensions 9 that contain a plurality of electrodes 2, FIG. 4. In order to tap, rub, or apply pressure in between said plurality of electrodes 2, said plurality of extensions 9 extend from the skin-puncturing means 1 so as to position said plurality of electrodes 2 in the vicinity of the puncture site and to allow tapping, applying pressure or rubbing, manually or otherwise, the area at or near the puncture site clear from the body of said skin-puncturing means 1. In an example of the invention, said plurality of extensions 9 are retractable into or next to the body of said skin-puncturing means 1 to give a compact appearance to the skin-puncturing means 1 preferably when not in use.

Figure 5:
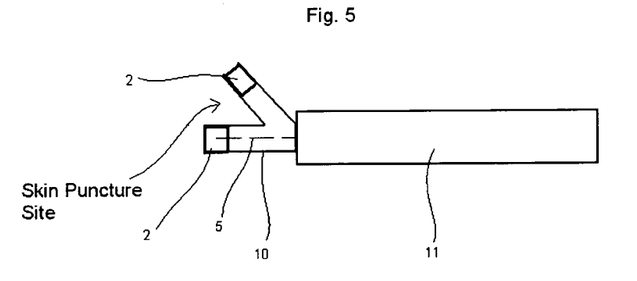
FIG. 5 shows that the extension can occur on the protective cap placed on the sharp object of the skin-puncturing means.

In a specific example of the invention, said skin-puncturing means 1 includes a cap 10 that protects the sharp edge of the puncturing means, for example, the needle 5 of a syringe 4 or the blade 7 of the lancet 6. Said cap 10 may include a plurality of said extensions 9, FIG. 5.

Figure 6:
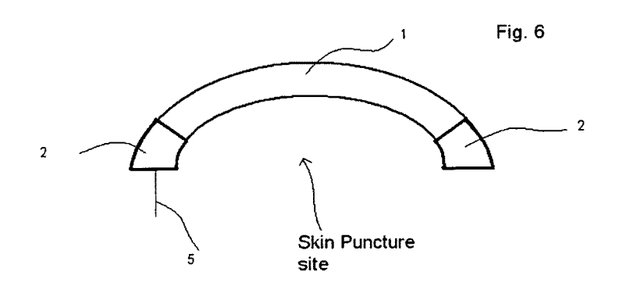
FIG. 6 illustrates a skin-puncturing means which is shaped so as to form a clear space, on the skin generally directly in between a plurality of electrodes, for directly tapping and applying pressure onto.

In a specific example of the invention, at least part of the body of said skin-puncturing means 1, which includes at least one said electrode 2, is not aligned in a straight line with the other parts of said puncturing means 1, FIG. 6. At least one said electrode 2 is located at a different part of said skin-puncturing means 1. This design allows for tapping, rubbing, or applying pressure in between said plurality of electrodes 2 clear from the body of said puncturing means 1 before, during, or after applying an electric current in the vicinity of the skin puncture to obtain local anesthesia.

In a specific example of the invention, said skin-puncturing means 1 includes a plurality of electrodes 2 positioned in contact with, and applying electrical impulses to, the skin. While a plurality of said electrodes 2 contact the skin, one taps on or presses on said skin-puncturing means 1 which then transfers the tapping forces, or pressure, to the skin at or in the vicinity of the puncture site, FIG. 7. After repeating the above step a few times, local anesthesia is obtained. One holds said skin-puncturing means 1 and painlessly inserts said sharp object included on said skin-puncturing means 1 into the skin and the underlying tissues.

In a specific example of the invention, said skin-puncturing means 1 includes a plurality of electrodes 2, mounted thereon, and positioned to be in contact with, and applying electrical impulses to, the skin. While a plurality of said electrodes 2 contact the skin, one moves said skin-puncturing means 1 on the skin thereby rubbing the skin at or in the vicinity of the puncture site, with said skin-puncturing means 1, FIG. 10. After repeating the above step a few times, local anesthesia is obtained. One holds said skin-puncturing means 1 and painlessly inserts said sharp object included on said skin-puncturing means 1 into the skin and the underlying tissues. In a specific example of the invention, said plurality of electrodes 2 bulge out to enhance the electrical contact with the skin, as well as improve the physical stimulation of rubbing the skin. In a preferred example of the invention, said plurality of electrodes 2 are springy in nature or are mounted on a plurality of electrode springs 14 to maintain contact with the skin while said plurality of electrodes 2 move on contours of the skin.

Figure 7:
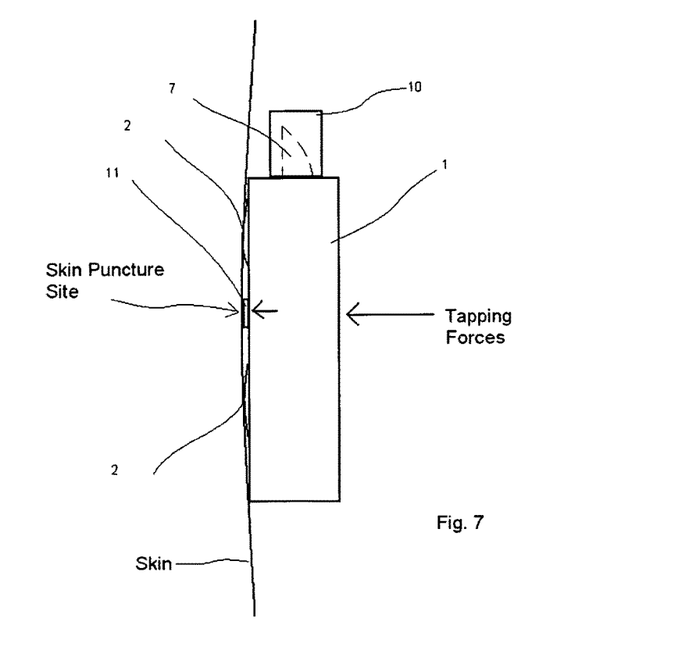
FIG. 7 shows a skin-puncturing means placed over the skin with its plurality of electrodes touching and applying electricity to the skin. It also includes a plurality of projections facing the skin. When the skin-puncturing means is tapped, or pressed, on, the tapping forces and the pressure are transmitted through the skin-puncturing means onto the skin.

In a specific example of the invention, said skin-puncturing means includes a plurality of projections 11 protruding from the body of said puncturing means 1 that are generally directed towards the skin. When placed on the skin, said projections 11 facilitate transferring the tapping forces, or pressure, to the skin when said skin-puncturing means 1 is tapped on or pressed onto the underlying skin. In a preferred embodiment of the invention, said plurality of electrodes 2 have a springy consistency and are raised from the body surface of said puncturing means 1 to help maintain electrical contact with the skin, when said plurality of electrodes 2 are placed on the skin. In a specific example of the invention, a plurality of said projections 11 act as a plurality of electrodes 2 that come in electrical contact with the skin. Therefore, said plurality of projections 11 transfer the tapping forces or the pressure exerted on said skin-puncturing means 1, as well as the electrical current to the underlying skin in order to obtain local anesthesia.

In a preferred method of obtaining local anesthesia, use is made of the disclosed skin-puncturing means 1 which includes an electric source 3 electrically connected to a plurality of electrodes 2 via a plurality of wires 12. Said plurality of electrodes 2 are electrically connected to the skin in the vicinity of the skin puncture. Then the skin on or around the puncture site is tapped before, during, or after electrical impulses are applied to the skin by said plurality of electrodes 2 for a period of time before the skin is punctured with a sharp object. In an example of the invention, instead of tapping the skin, pressure is applied over the skin before, during, or after electrical impulses are applied to the skin by said plurality of electrodes 2 in order to obtain local anesthesia. In another example of the invention, instead of tapping the skin, the skin is rubbed before, during, or after electrical impulses are applied to the skin by said plurality of electrodes 2 in order to obtain local anesthesia.

In a different preferred method of obtaining local anesthesia, after applying said plurality of electrodes 2 to the skin in the vicinity of the puncture site, the body of said skin-puncturing means 1 is tapped on the skin at or near the puncture site before, during, or after electrical impulses are applied to the skin by said plurality of electrodes 2 for a period of time before the skin is punctured with a sharp object. In one example of the invention, instead of tapping the skin, pressure is applied on the skin with the body of said skin-puncturing means 1. In a different method, pressure is applied over a plurality of said electrodes 2 which then exert pressure over the skin. In another example of the invention, instead of tapping the skin, the skin is rubbed with the body of said skin-puncturing means 1. In yet a different method, specifically, a plurality of said electrodes 2 mounted on said skin-puncturing means 1 are what actually rub the skin.

In another preferred method of obtaining local anesthesia, said skin-puncturing means contains a plurality of springs 8, attached to said plurality of electrodes 2, that help stabilize said plurality of electrodes 2 over the skin during the back and forth motion of said skin-puncturing means 1 to exert pressure or tapping forces on, or rub, the skin at or near the puncture site.

In yet another preferred method of obtaining local anesthesia, said skin-puncturing means 1 includes a plurality of extensions 9, carrying a plurality of electrodes 2, that can extend out of the body of said skin-puncturing means 1 so that said plurality of electrodes 2 make electrical contact with the skin away from the body of said skin-puncturing means 1 to provide space, clear from the body of said skin-puncturing means 1, in between a plurality of electrodes 2, onto which then tapping is administered, pressure is applied, or rubbing is performed directly on the skin.

Furthermore, a method of obtaining local anesthesia is disclosed including rubbing the skin before, during, or after application of an electric impulse in the vicinity of a puncture site followed by insertion of a sharp object into the skin.

One skilled in the art will appreciate that the present invention can be practiced by other than the described embodiments, which are presented here for purposes of illustration and not of limitation, and the present invention is limited only by the claims that follow.

What I claim is:

1. A method of diminishing or removing pain of a skin puncture including
   a. rubbing side to side repeatedly, on a skin puncture site or a vicinity of said skin puncture site at least before, during, or after the skin puncture and
   b. applying electricity by a plurality of electrodes to said skin puncture site or the vicinity of said skin puncture site at least before, during, or after said skin puncture.
2. The method according to claim 1 wherein said rubbing is performed back and forth.
3. The method according to claim 2 wherein said rubbing is performed by a syringe or a lancet that includes said plurality of electrodes.
4. The method according to claim 3 wherein said syringe is an auto-injecting syringe.
5. The method according to claim 1 wherein said rubbing is performed on said skin puncture site.
6. The method according to claim 1 wherein said rubbing is performed on skin in between the plurality of electrodes.
7. The method according to claim 6 wherein the skin puncture site is closer to where said rubbing is performed than to where the plurality of electrodes are placed.
8. The method according to claim 1 wherein said rubbing is performed by said plurality of electrodes.
9. The method according to claim 1 wherein said rubbing is performed by moving on skin on or near said skin puncture site a means with which to rub the skin.
10. The method according to claim 1 wherein said electricity is applied before said skin puncture.
11. The method according to claim 1 wherein said rubbing is performed before said skin puncture.
12. A method of diminishing or removing pain of a skin puncture including
    a. rubbing side to side repeatedly, on a skin puncture site or a vicinity of said skin puncture site before the skin puncture and
    b. applying electricity by a plurality of electrodes to said skin puncture site or the vicinity of said skin puncture site before and during the skin puncture.
13. A method of diminishing or removing pain of a skin puncture by applying electricity to a first area of skin near a skin puncture site and stopping said applying electricity before the skin puncture, and rubbing repeatedly, side to side, on a second area of the skin at or near the skin puncture site and stopping said rubbing before the skin puncture, wherein the second area of the skin is closer to the skin puncture site than the first area of the skin.
14. The method according to claim 13 wherein said rubbing is performed at least on said skin puncture site.
15. The method according to claim 13 wherein said rubbing is performed by moving on the skin on or near said skin puncture site a means with which to rub the skin.
16. The method according to claim 13 wherein said rubbing is performed by moving a means with which to rub the skin.
17. A method of diminishing or removing pain of a skin puncture by a syringe or a lancet having a first side and a second side and including a needle or a blade disposed on the first side and a plurality of electrodes disposed on the second side, said method including
    a. rubbing side to side repeatedly, on a skin puncture site or a vicinity of said skin puncture site before the skin puncture;
    b. with the second side facing the skin puncture site and said plurality of electrodes making electric contact with skin, applying electricity by said plurality of electrodes to said skin puncture site or the vicinity of said skin puncture site before the skin puncture,
c. reorienting said syringe or said lancet so that the first side faces the skin puncture site and said electric contact is disrupted; and
d. puncturing the skin puncture site with the needle or the blade.

* * * * *